(12) United States Patent
Xu et al.

(10) Patent No.: US 10,696,748 B2
(45) Date of Patent: Jun. 30, 2020

(54) HYBRIDOMA CELL LINE OF SECRETING CLARITHROMYCIN MONOCLONAL ANTIBODIES AND PREPARATION METHOD THEREOF

(71) Applicant: JIANGNAN UNIVERSITY, Wuxi, Jiangsu (CN)

(72) Inventors: Chuanlai Xu, Wuxi (CN); Hua Kuang, Wuxi (CN); Lu Zeng, Wuxi (CN); Liguang Xu, Wuxi (CN); Liqiang Liu, Wuxi (CN); Shanshan Song, Wuxi (CN); Xiaoling Wu, Wuxi (CN); Yongming Hu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/394,982

(22) Filed: Apr. 25, 2019

(65) Prior Publication Data
US 2019/0284304 A1    Sep. 19, 2019

Related U.S. Application Data

(62) Division of application No. 16/222,792, filed on Dec. 17, 2018, now Pat. No. 10,323,100.

(30) Foreign Application Priority Data

Mar. 16, 2018 (CN) .......................... 2018 1 0219848

(51) Int. Cl.
*C07K 16/44* (2006.01)
*A61K 31/7048* (2006.01)
*C12N 5/12* (2006.01)
*C07K 16/06* (2006.01)

(52) U.S. Cl.
CPC .......... *C07K 16/44* (2013.01); *A61K 31/7048* (2013.01); *C07K 16/065* (2013.01); *C12N 5/12* (2013.01); *C07K 2317/92* (2013.01)

(58) Field of Classification Search
None
See application file for complete search history.

(56) References Cited

FOREIGN PATENT DOCUMENTS

| CN | 106588857 A | 4/2017 |
|----|-------------|--------|
| CN | 106589024 A | 4/2017 |

OTHER PUBLICATIONS

Yokoyama, Production of Monoclonal Antibodies, Current Protocols in Cell Biology, 161.1-161.17, 1999.*
Galvidis, I, G. Lapa, and M. Burkin. "Group determination of 14-membered macrolide antibiotics and azithromycin using antibodies against common epitopes." Analytical Biochemistry 468(2015):75-82.

* cited by examiner

*Primary Examiner* — Brian Gangle
(74) *Attorney, Agent, or Firm* — Enshan Hong; VLP Law Group LLP

(57) ABSTRACT

A hybridoma cell line of secreting clarithromycin monoclonal antibodies with a preservation number of hybridoma cell line of CGMCC No. 14696 belongs to the field of food safety immunological detection. BALB/c mice are immunized through one time immunization with complete freund's adjuvant, three times of booster immunization with incomplete freund's adjuvant and one time of rush immunization with clarithromycin complete antigen without adjuvant; the spleen cells from BALB/C mice immunized with high potency and low value of IC50 are fused with murine myeloma cells; and then the hybridoma cell line is obtained through indirect competitive ELISA screening and three subclones. The monoclonal antibody secreted by this cell line has good specificity and detection sensitivity to clarithromycin (value of IC50 is 0.3 ng/ml), being suitable for detection of clarithromycin in food.

3 Claims, 1 Drawing Sheet

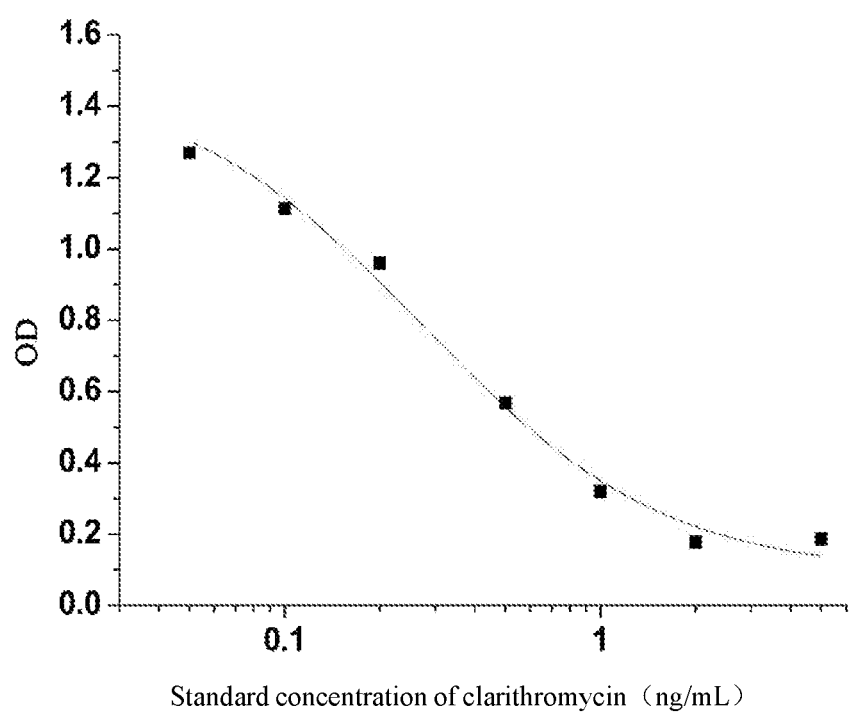

HYBRIDOMA CELL LINE OF SECRETING CLARITHROMYCIN MONOCLONAL ANTIBODIES AND PREPARATION METHOD THEREOF

CROSS-REFERENCES TO RELATED APPLICATIONS

This application is a divisional application of U.S. patent application Ser. No. 16/222,792 filed Dec. 17, 2018, which claims priority from China Patent Application Serial Number 201810219848.1, which was filed on Mar. 16, 2018, the entire content of which is incorporated herein as reference.

BACKGROUND OF THE INVENTION

1. Technical Field

The invention relates to the technical field of food safety and immunological detection, in particular to a hybridoma cell line of secreting clarithromycin monoclonal antibodies and preparation method thereof.

2. Background Art

Clarithromycin (CLA) belongs to macrolide antibiotic, which is the second generation of erythromycin. It has stability and strong sterilization ability which has the strong germicidal effect on most gram-positive bacteria, some gram-negative bacteria and some mycoplasma chlamydia. Therefore, CLA is widely used in the treatment of respiratory tract, wound, genitourinary system infection. As a result, many poor manufacturers illegally added the drug to the drinking or feeding for animals to increase the animal survival rate and gain illegal profits.

However, this illegal behavior can lead to drug residues in animals, where clarithromycin accumulates in large quantities. These drugs will accumulate in people's bodies, who eat these animals. Long-term continuous intake of clarithromycin could cause nausea, heartburn, abdominal pain, diarrhea and headache. It also causes drug fever, drug eruption, urticaria and other allergic reactions In addition, it has side effect on the central nervous system seriously endangering human health. Therefore, we urgently need to find a highly specific and sensitive method to detect clarithromycin residues in food.

At present, the detection methods of clarithromycin are mainly Gas Chromatography (GC), High-Performance Liquid Chromatography (HPLC), Gas Chromatography-Mass Spectrometer (GC-MS) and Liquid Chromatography-Mass Spectrometry (LC-MS). However, these methods require expensive instruments, professional operators, and complex pretreatment of samples, which would cause high cost and time-consuming, which is hard to realize rapid detection of a large number of samples. Therefore, it is of great significance to establish a rapid and simple detection method.

Enzyme-linked immunoassay (ELISA) is a kind of extremely efficient, sensitive and rapid detection methods, which has lower requirements for the purity of the sample and easy to operate, being suitable for spot rapid diagnosis with a large number of samples, however, the premise of using enzyme-linked immunoassay detection is that the monoclonal antibody is available, which has high specificity and sensitivity to clarithromycin. Therefore, it is very important to find a method to prepare monoclonal antibody with high specificity and sensitivity to clarithromycin.

The inventor tried to prepare the clarithromycin monoclonal antibody through the hybrid tumor cells. However, in the process of preparing hybrid tumor cell lines which has capable of secreting clarithromycin monoclonal antibodies, it is needed to further study that how to prepare clarithromycin complete antigen and establish mouse immunity, it is needed to be further verified that whether the prepared hybrid tumor cell line can secrete clarithromycin monoclonal antibody, the specificity and sensitivity of the clarithromycin monoclonal antibody are also needed to be further verified.

SUMMARY OF THE INVENTION

The purpose of the present invention is to obtain a kind of hybridoma cell line of secreting clarithromycin monoclonal antibodies and preparation method thereof. A clarithromycin monoclonal antibody secreted by a hybrid tumor cell line was obtained in application of this invention and has high specificity and sensitivity (IC50 value concentration of 0.3 ng/ml), and the minimum detection limit of determination of clarithromycin by hplc-ms is 2 ng/mL, as a result, the method provided in the present invention can be used to establish an immunological detection method for clarithromycin and to detect clarithromycin residues in food.

The invention provides a hybrid tumor cell line that secretes clarithromycin monoclonal antibody, which has been deposited with the general microbiological center of China General Microbiological Culture Collection Center (No. 1 West Beichen Road, Chaoyang District, Beijing, China) under Accession Number CGMCC No. 14696.

The present invention provides a preparation method for a hybrid tumor cell line that secretes clarithromycin monoclonal antibody, and contains the following steps:

Step 1: Clarithromycin haptens and clarithromycin complete antigens are prepared, and the obtained clarithromycin complete antigen is prepared as freund's adjuvant and incomplete freund's adjuvant.

Step 2: The obtained freund's adjuvant was injected into BALB/c mice for several times for immunization subcutaneously through the back. Complete freund's adjuvant is used for the first time for immunization, while incomplete freund's adjuvant is used to strengthen immunity.

Step 3: Blood samples were taken from the mice after the above immune process, and the serum immune titer and immunosuppressive ability were detected by indirect ELISA to select the mice with high serum clarithromycin antibody content.

Step 4: The selected mice were subjected to one last booster immunization with Incomplete Freund's adjuvant, and then, the impact immunity is performed via intraperitoneal injection, using clarithromycin complete antigen without freund's adjuvant.

Step 5: The spleen cells and myeloma cells of BALB/c mice after impact immunity are fused by polyethylene glycol (PEG4000) method, and the fusion cells cultured on HAT medium. The inhibitory effect of positive cell pores are detect by indirect competitive inhibition ELISA, and three subclones of positive cells with the best inhibition were performed by limited dilution method, and eventually the hybrid tumor cell line that secretes a monoclonal antibody to clarithromycin get screened.

Step 6: The sensitivity and specificity of the antibody secreted by hybrid tumor cell lines that secrete clarithromycin monoclonal antibodies were determined by indirect ELISA.

The molecular formula of clarithromycin hapten in step 1 is as follows:

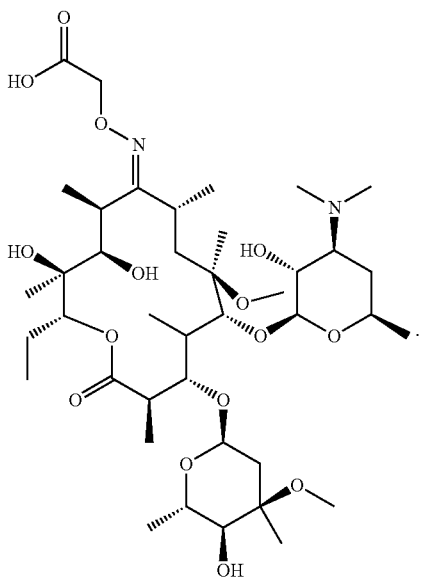

The molecular formula of clarithromycin antigen in step 1 is as follows:

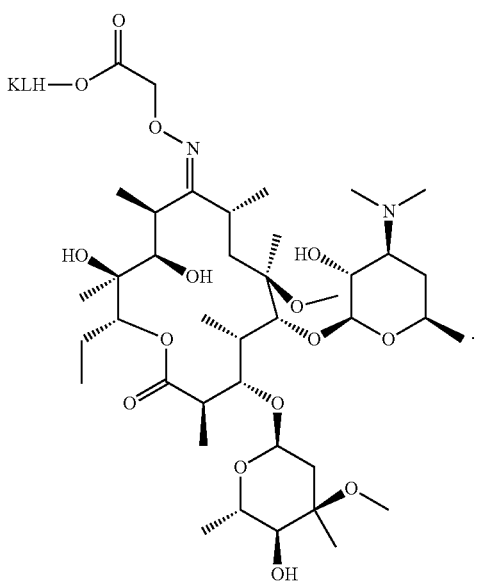

In one embodiment, in step 2 and step 4, the interval between the first immunization and the booster immunization is one month, the interval between the booster immunization is 21 days, and the interval between the booster immunization and the rush immunization is 21 days.

In another embodiment, in step 2 and step 4, primary immune dose is 100 μg/mouse, booster immune dose is 50 μg/mouse, rush immunization dose is 25 μg/mouse.

In a further embodiment, in step 2 and step 4. In a further embodiment, the immune process includes 1 time immunization, 4 times booster immunization and 1 time shock immunization in step 2 and step 4.

In another embodiment, blood collection was conducted 7 days after the end of the 3rd immune process in step 3.

In another embodiment, cell fusion is carried out 3 days after the end of shock immunity.

The present invention provides an application of a hybridoma cell line that can be used to prepare clarithromycin monoclonal antibody.

The present invention provides a clarithromycin hapten with the formula as follows:

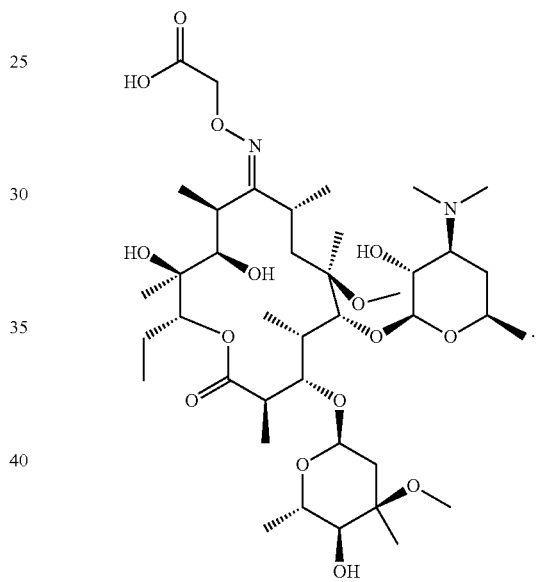

In another embodiment, the clarithromycin hapten is obtained through the equation is as follows:

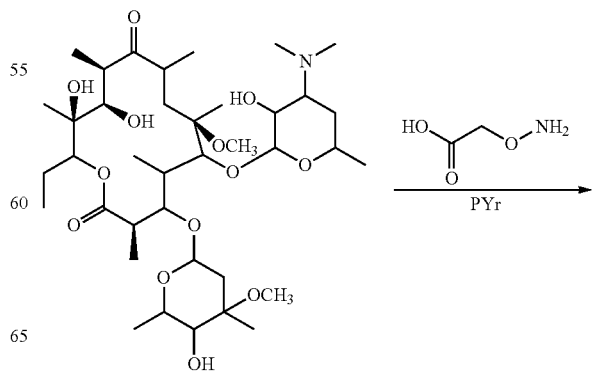

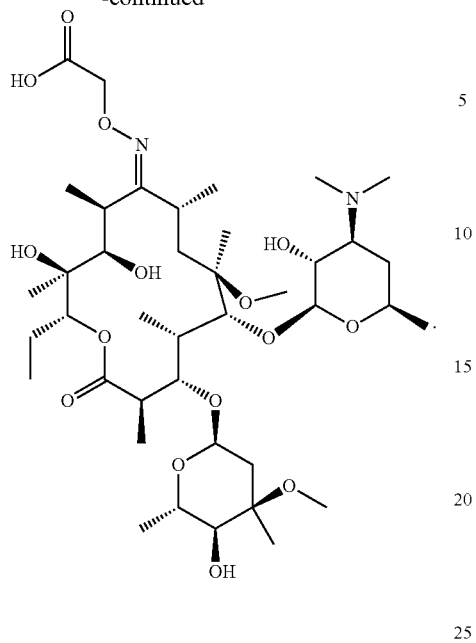

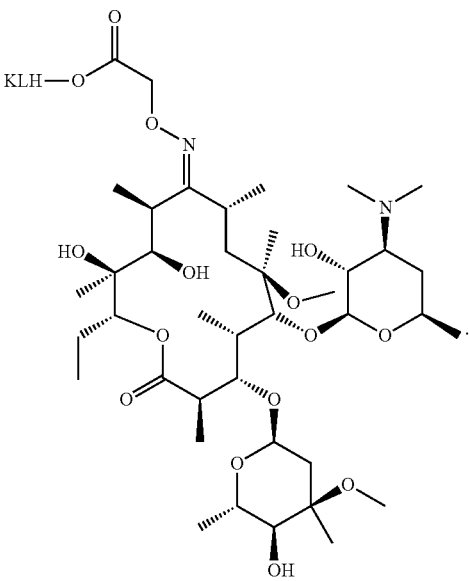

The invention provides a preparation method of clarithromycin hapten. The carboxymethoxylamine hemihydrochloride (CMO) is added to the mixture that the clarithromycin (CLA) was fully dissolved in anhydrous pyridine. The mixture is stirred in the water bath avoiding light, and then being activated. After the reaction, the mixture is dried by nitrogen and dissolved in methanol solution, using ethyl acetate to extract three times, and the organic phase was merged removing with the helping of the rotary evaporation, obtaining white snowflake solid that is hapten CLA-CMO.

In one embodiment, clarithromycin (CLA) 100 mg fully dissolved in anhydrous pyridine 10 mL, adding and stirring in 29.2 mg carboxymethoxylamine hemihydrochloride (CMO). The mixture is using water bath in 37° C. and avoid light. After 5 h finishing activation, the mixture is dried by nitrogen and dissolved in 8 mL methanol solution, using 10 mL ethyl acetate to extract three times, and the organic phase was merged removing with the helping of the rotary evaporation, obtaining white snowflake solid that is hapten CLA-CMO.

The invention provides an application of a clarithromycin hapten. this haptens can be used for preparation of clarithromycin complete antigen, clarithromycin antibody and hybridoma cell strain of secreting clarithromycin monoclonal antibody.

The present invention provides a clarithromycin complete antigen with the formula as follows:

In one embodiment, the clarithromycin complete antigen is obtained through the equation is as follows:

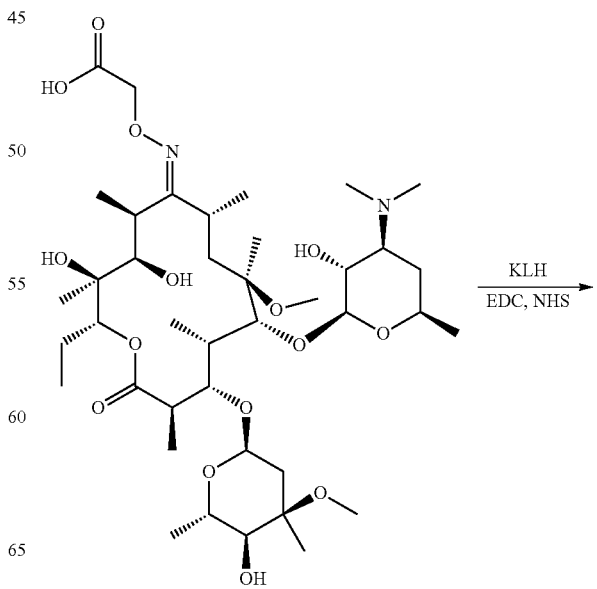

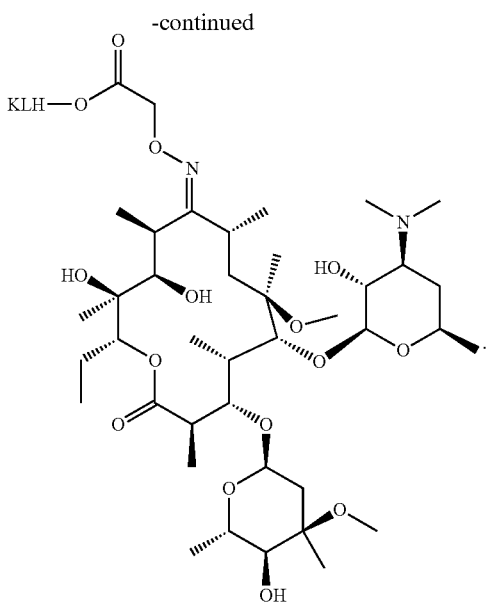

The present invention provides a preparation method of clarithromycin complete antigen, the CLA-CMO, 1-ethylene-(3-dimethylaminopropyl) carbodiimine hydrochloride (EDC) and n-hydroxysuccinylimide (NHS) are dissolved with anhydrous N, n-dimethylamine and activated at room temperature. The CLA-CMO solution after activation is slowly added to the keyhole limpet hemocyanin (KLH) solution dropwise. After the stirring at room temperature overnight, the CLA-CMO-KLH complete antigen mixture is obtained, dialysis and identified.

In one embodiment, 10.8 mg the CLA-CMO, 7.56 mg 1-ethylene-(3-dimethylaminopropyl) carbodiimine hydrochloride (EDC) and 4.56 mg n-hydroxysuccinylimide (NHS) are dissolved with 800 uL anhydrous N,N-dimethylamine and activated at room temperature. The CLA-CMO solution after 8 h activation is slowly added to the keyhole limpet hemocyanin (KLH) solution dropwise. After the stirring at room temperature overnight, the CLA-CMO-KLH complete antigen mixture is obtained, dialysis under 4° C. for 3 days to isolate complete antigen and uncoupled small molecule haptens, and then complete antigen is identified by uv absorption scanning.

The invention provides an application of clarithromycin antigen, this antigens can be used preparation of clarithromycin antibodies and the preparation of hybrid tumor cell lines of secreting monoclonal antibodies of clarithromycin.

The present invention provides a clarithromycin monoclonal antibody, which the antibody is obtained from a hybrid tumor cell line with the preservation number CGMCC no. 14696.

The invention provides a preparation method of clarithromycin monoclonal antibody, BALB/c mice were intraperitoneally injected with paraffin oil, and then intraperitoneally injected with hybrid tumor cells secreting clarithromycin monoclonal antibody. After injection, ascites were collected and purified, then the monoclonal antibody was preserved at low temperature.

In another embodiment, BALB/c mice with 8 to 10 weeks, were intraperitoneally injected with paraffin oil 1 mL each. After 7 days, each mouse intraperitoneally is injected with $1 \times 10^6$ hybrid tumor cells secreting clarithromycin monoclonal antibody.

From 7 days start collecting ascites, purified by bitter-ammonium sulfate law, the monoclonal antibody was preserved at −20° C.

The present invention provides an application of clarithromycin monoclonal antibody, which can be applied to specifically identify clarithromycin.

The present invention provides a test kit for the preparation of the product of the hybrid tumor cell line that secretes clarithromycin monoclonal antibody.

The present invention provides a detection kit prepared from the above clarithromycin hapten.

The present invention provides a detection kit prepared from the above clarithromycin antigen.

The present invention provides a detection kit prepared from the above monoclonal antibody of clarithromycin.

The advantages of the invention are:
1. The monoclonal antibody cell line obtained by the invention has a good detection sensitivity and specificity for clarithromycin (IC50 value is 0.3 ng/ml); the content of clarithromycin was determined by HPLC-MS with a minimum detection limit of 2 ng/mL.
2. The monoclonal antibody cell lines obtained by the present invention can be used for immunoassay detection.

Preserve Biological Materials

A hybrid tumor cell line that secretes monoclonal antibodies to clarithromycin, which the classification is called monoclonal cell lines, has been deposited with the general microbiological center of the China General Microbiological Culture Collection Center (No. 1 West Beichen Road, Chaoyang District, Beijing, China) under Accession Number CGMCC No. 14696 at Sep. 5, 2017.

BRIEF DESCRIPTION OF THE DRAWINGS

FIG. 1 shows the standard curve of the monoclonal antibody inhibition.

DESCRIPTION OF PREFERRED EMBODIMENTS

The detailed implementation of the invention is further described as follows. The following embodiments are used to illustrate the invention, but not to limit the scope of the invention.

EXAMPLE 1

Synthesis of Clarithromycin Complete Antigen

1. Synthesis of haptens: clarithromycin (CLA) 100 mg fully dissolved in anhydrous pyridine 10 mL, adding and stirring in 29.2 mg carboxymethoxylamine hemihydrochloride (CMO). The mixture is using water bath in 37° C. and avoid light. After 5 h finishing activation, the mixture is dried by nitrogen and dissolved in 8 mL methanol solution, using 10 mL ethyl acetate to extract three times, and the organic phase was merged removing with the helping of the rotary evaporation, obtaining white snowflake solid that is hapten CLA-CMO.

2. Complete antigen synthesis: 10.8 mg the CLA-CMO, 7.56 mg 1-ethylene-(3-dimethylaminopropyl) carbodiimine hydrochloride (EDC) and 4.56 mg n-hydroxysuccinylimide (NHS) are dissolved with 800 uL anhydrous N,N-dimethylamine and activated at room temperature. The CLA-CMO solution after 8 h activation is slowly added to the keyhole limpet hemocyanin (KLH) solution dropwise. After the stirring at room temperature overnight, the CLA-CMO-KLH complete antigen mixture is obtained, dialysis under 4° C. for 3 days to isolate complete antigen and uncoupled small molecule haptens, and then complete antigen is identified by uv absorption scanning.

EXAMPLE 2

Preparation of Hybrid Tumor Cell Lines That Secrete Clarithromycin Monoclonal Antibodies 1. Animal Immunization Healthy Balb/C mice aged 6-8 weeks were selected for immunization. The obtained clarithromycin complete antigen was mixed with the same amount of oil agent, adding the emulsifier, and then the incomplete freund's adjuvant was obtained. Complete freund's adjuvant was obtained by adding mycobacterium into incomplete freund's adjuvant. The obtained freund's adjuvant was injected subcutaneously into the back to immunize BALB/c mice for several times. The first immunization was performed with complete freund's adjuvant, the second booster immunization was performed with the indeterminate freund's adjuvant, and 7th day after the third immunization was finish. The blood of mice was collected, the serum immune titer and immunosuppression ability of mice were detected by indirect ELISA, and selecting immunized mice with high serum levels of clarithromycin antibodies. The two more booster immunization was performed with incomplete Freund's adjuvant in the selected mice. Then the clarithromycin complete antigen without adjuvant was used for rush immunization by intraperitoneal injection were immunized with clarithromycin complete antigen without adjuvant. No adjuvant was used, and intraperitoneal injection was used (the interval between booster immunization was 21 days, the interval between booster immunization and rush immunization was 18 days, the dose of the first immunization was 100 μg/mouse, the dose of the booster immunization was 50 μg/mouse, the dose of the rush immunization was 25 μg/mouse).

Measuring the serum of mice immunized at 3, 4 and 5 times, the results showed that when the serum was diluted 3000 times and the clarithromycin was added with 10 ng/mL, OD450 nm was 1.405, 1.785 and 2.012 respectively, the inhibition rate was 55%, 68% and 78% respectively, which meant the higher efficiency and inhibition rate can be obtained by increasing the number of immunization times.

1. Cell Fusion

After 3 days of shock immunity, cell fusion was performed by PEG (polyethylene glycol, with a molecular weight of 1500). The steps are as follows:

(1) After mice were killed by cervical dislocation, their eyeball blood was picked and soaked immediately in 75% alcohol disinfection about 5 min. The spleen of the mice was taken out by aseptic operating, grinded moderately by the glue head of the syringe and gotten the splenocyte suspension through 200 mesh cell screen. And the splenocyte suspension was collected and centrifuged (1200 RPM, 8 min). And then washing spleen cells three times with RPMI-1640 medium, after the last time the centrifugal, spleen cells were diluted to a certain volume, count, and standby application.

Collect sp2/0 cells: Sp2/0 tumor cells were cultured in 5% $CO_2$ culture box with RPMI-1640 medium containing 10% FBS (fetal bovine serum) between 7 and 10 days before fusion. Before fusion, the number of sp2/0 tumor cells was required to reach $1-4 \times 10^7$, ensuring that sp2/0 tumor cells were in the logarithmic growth stage. At the time of fusion, tumor cells were collected and suspended in rpm-1640 basic medium for cell counting.

The fusion process lasted for 7 min. During the first min. 1 mL of PEG1500 was added to the cells from slow to fast. For the second minute, there was stewing. For the three and four minutes, culture medium of 1 ml RPMI-1640 was added within 1 min. For the five and six minutes, Culture medium of 2 m RPMI-1640 was added within 1 min. For the seven minute, 1 mL rpm-1640 culture medium was added every 10 s. Then the cells were under warm bath at 37° C. 5 min, abandoned supernatant through centrifugation (800 rpm, 8 min), resuspended with 20% fetal bovine serum. And then 2% of the 50×HAT RPMI-1640 filter medium added to 96 hole cell plate according to the 200 μL/hole, at 37° C. and 5% $CO_2$ incubator to cultivate.

1. Cell Screening and Cell Line Establishment

On the third day of cell fusion, the fusion cells were partially replaced with the rpm-1640 screening medium, and on the fifth day, the cells were fully replaced with the rpm-1640 transition medium containing 20% fetal bovine serum and 1% 100×HT, and the supernatant was taken on the seventh day for screening.

Screening is divided into two steps: the first step was to screen out the positive cells by indirect ELISA; in the second step, clarithromycin was selected as the standard product, and the inhibitory effect of positive cells was measured by indirect competitive ELISA. Cell pores that had good inhibition on all clarithromycin standard products were selected, and subclone was conducted by finite dilution method. The same method was used for detection, and the cell lines were obtained after repeated for three times.

Cryopreservation of Cell Line

This cell line called monoclonal antibodies had been deposited with the general microbiological center of the China General Microbiological Culture Collection Center under Accession Number CGMCC No. 14696 at Sep. 5, 2017.

EXAMPLE 3

Preparation and identification of clarithromycin monoclonal antibody BALB/c mice with 8 to 10 weeks, were intraperitoneally injected with paraffin oil 1 mL each. After 7 days, each mouse intraperitoneally is injected with $1 \times 10^6$ hybrid tumor cells secreting clarithromycin monoclonal antibody. From 7 days start collecting ascites, purified by bitter-ammonium sulfate law, in the condition of partial acid, n-caprylic acid can precipitate other heterologous proteins except IgG immunoglobulin in ascites, and then the precipitation was discarded after centrifuge. The monoclonal antibody of IgG type was precipitated with ammonium sulfate solution of equal saturation, and then the supernatant was discarded after centrifuge. After dissolving precipitate with 0.01 MPBS solution (pH7.4), being desalination through dialysis, finally, the monoclonal antibody was obtained after purification and preserved at −20° C.

IC50 of the monoclonal antibody clarithromycin was 0.3 ng/ml using indirect competitive ELISA, indicating a good sensitivity to clarithromycin and can be used for clarithromycin immunoassay (the standard curve of inhibition of monoclonal antibody is shown in FIG. 1).

EXAMPLE 4

Application of Clarithromycin Monoclonal Antibody

The monoclonal antibodies obtained from hybrid tumor cells secreting clarithromycin were applied to the ELISA recovery test of clarithromycin, and the specific steps are as follows:

Solution configuration: Carbonate buffer (CBS): 1.59 g Na2CO3, 2.93 g NaHCO3 were weighed and taken, and dissolved in a small amount of double distilled water respectively, then added double distilled water to about 800 ml water, blending and adjusting pH value to 9.6, fill double distilled water to 1000 ml with double distilled water, keeping 4° C. storage for later use.

Phosphate buffer (PBS): 8.00 gNaCl, 0.2 g KCl, 0.2 g $KH_2PO_4$, 2.9 g $Na_2HPO_4 \cdot 12H_2O$, dissolved in 800 mL pure water, with NaOH or HCl to adjust pH to 7.2~7.4, fill pure water to 1000 mL.

PBST: PBS with 0.05% tween 20.

TMB Color liquid: Solution A: $Na_2HPO_4 \cdot 12H_2O$ 18.43 g, citric acid 9.33 g, pure water, constant volume to 1000 mL; Solution B: 60 mgTMB is dissolved in 100 mL ethylene glycol. When A and B are mixed by a ratio of 1:5, the mixture was TMB chromogenic solution and used right after it was ready.

Coating: CLA-CMO-OVA was doubling dilution with 0.05 M pH9.6 carbonate buffer starting from 1 μg/mL, 100 uL/hole, 37° C. reaction 2 h Washing: Pour out the solution in the plate, dry it, and wash it 3 times with wash solution, 3 min each;

Sealing: After dried, adding in 200 uL/hole sealing fluid, and 37° C. reaction 2 h, drying alternate after washing;

Sample adding: The antiserum was diluted from 1:00 to 1:00, and added to each dilution degree of the packet hole, 100 uL/hole, 37° C. reaction 30 min; after washing fully, adding 1:3000 diluted HRP-sheep fight mouse IgG, 100 uL/hole, 37° C. reaction 1 min;

Color development: After the enzyme label plate was taken out and fully washed, 100 ul TMB chromogenic liquid was added to each hole, and the reaction was kept at 37° C. for 15 minutes.

Termination and determination: 50 uL terminated fluid was added to each hole to terminate the reaction, and then OD450 value of each hole was measured with enzyme standard.

The results of interpretation: Serum ELISA titer was defined as the highest serum dilution multiple corresponding to the serum with OD450 value greater than or equal to 2.1 times of the negative control hole (that is P/N greater than or equal to 2.1).

The IC50 of the monoclonal antibody clarithromycin was 0.3 ng/mL and the minimum detection limit was 0.05 ng/mL detected by ic-ELISA, indicating a good sensitivity to clarithromycin and can be used for clarithromycin immunoassay.

The above description is only a preferred method of implementation of the invention, and is not used to limit the invention. It should be noted that, for ordinary technical personnel in the field of technology, some improvements and variations can be made under the technical principles of the invention. These improvements and variations should also be considered as the scope of protection of the invention.

What is claimed is:

1. A method for preparing a hybrid tumor cell line of secreting clarithromycin monoclonal antibodies comprising:

step 1: a) coupling clarithromycin hapten with a carrier protein to obtain clarithromycin complete antigen, b) mixing the clarithromycin complete antigen with an oil and then an emulsifier to obtain incomplete Freund's adjuvant, and d) adding mycobacterium into an amount of the incomplete freund's adjuvant to obtain complete Freund's adjuvant;

step 2: first injecting the complete Freund's adjuvant into BALB/c mice for immunization subcutaneously through the back, and then injecting the incomplete Freund's adjuvant into the BALB/c mice multiple times to strengthen immunity,;

step 3: taking blood samples from the mice after the immunization process of step 2, and selecting mice with higher serum clarithromycin antibody content based on indirect enzyme-linked immunoassay (ELISA);

step 4: subjecting the selected mice to booster immunization with Freund's incomplete adjuvant, and then performing intraperitoneal injection, using the clarithromycin complete antigen without the Freund's complete or incomplete adjuvant;

step 5: after step 4, fusing spleen cells and myeloma cells of BALB/c mice by polyethylene glycol (PEG4000) method to obtain fused cells, culturing the fused cells on hypoxanthine-aminopterin-thymidine medium (HAT) medium, selecting positive cells by indirect competitive ELISA, performing three subclones of the positive cells with the best inhibition by limited dilution assays, and eventually screening the hybrid tumor cell line that secretes a monoclonal antibody to clarithromycin; and step 6: determining the sensitivity and specificity of the antibody secreted by the hybrid tumor cell line that secretes the clarithromycin monoclonal antibody by indirect ELISA;

wherein the molecular formula of clarithromycin hapten in step 1 is as follows:

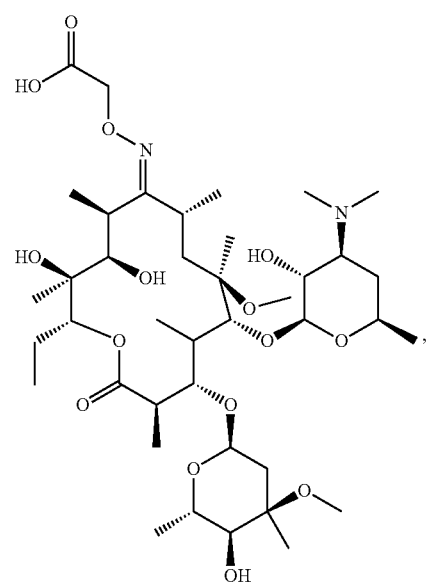

the molecular formula of clarithromycin complete antigen in step 1 is as follows:

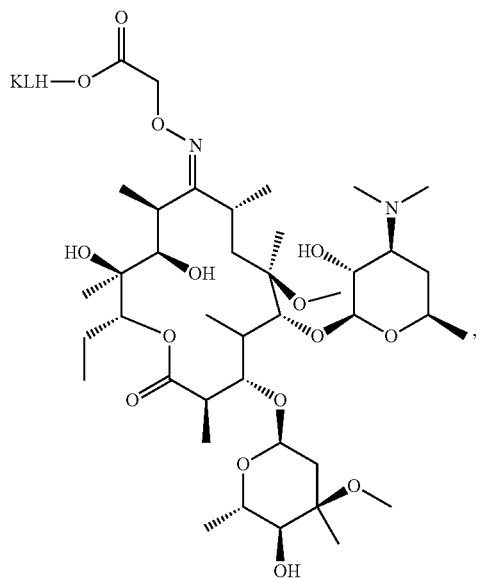

wherein KLH represents keyhole limpet hemocyanin.

2. The method of claim 1 comprising obtaining the clarithromycin hapten in step 1 through an equation as follows:

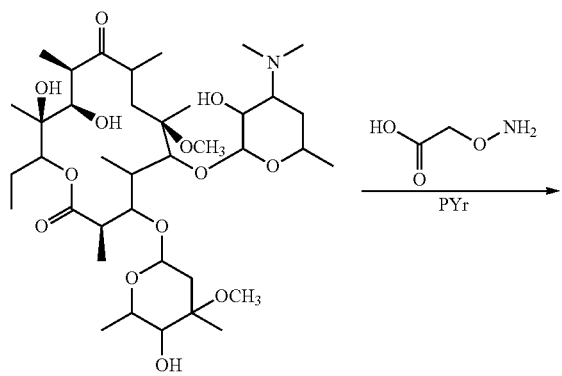

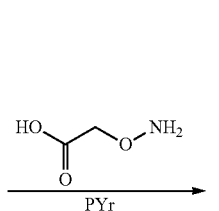

wherein PYr represents pyridine.

3. The method of claim 1 comprising obtaining the clarithromycin complete antigen through an equation as follows:

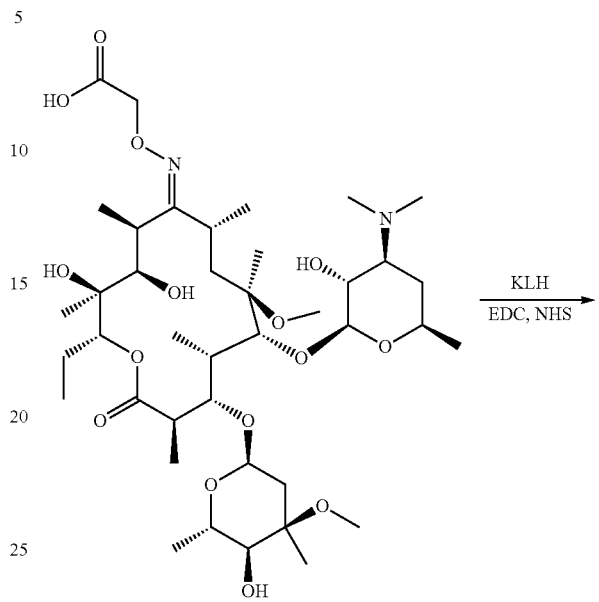

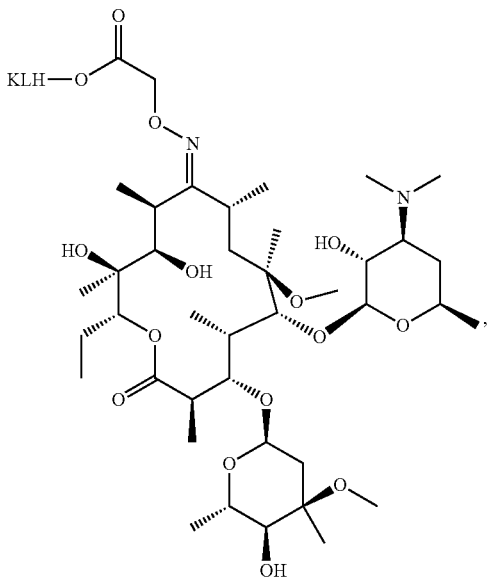

wherein KLH represents keyhole limpet hemocyanin, EDC represents 1-ethylene-(3-dimethylaminopropyl) carbodiimine hydrochloride, and NHS represents n-hydroxysuccinylimide.

* * * * *